United States Patent [19]

Dixon

[11] 4,191,738
[45] Mar. 4, 1980

[54] IMMUNOASSAY FOR N-DESMETHYLDIAZEPAM

[75] Inventor: William R. Dixon, Dumont, N.J.

[73] Assignee: Hoffmann-La Roche Inc., Nutley, N.J.

[21] Appl. No.: 894,279

[22] Filed: Apr. 7, 1978

[51] Int. Cl.² .................... G01N 33/16; A61K 43/00; A61K 39/00; G21H 5/02
[52] U.S. Cl. .................................. 424/1; 260/112 B; 260/239.3 R; 424/12; 424/8; 23/230 B
[58] Field of Search ................ 260/239.3 R, 112 B; 424/1, 12, 8; 23/230 B

[56] References Cited

U.S. PATENT DOCUMENTS

| | | | |
|---|---|---|---|
| 3,966,764 | 6/1976 | Goldstein et al. | 260/239.3 R |
| 4,058,511 | 11/1977 | Singh | 424/12 |

Primary Examiner—Benjamin R. Padgett
Assistant Examiner—Christine M. Nucker
Attorney, Agent, or Firm—Jon S. Saxe; George M. Gould; James H. Callwood

[57] ABSTRACT

Highly specific antibodies to N-desmethyldiazepam are obtained by using as an immunogen 4'-hydrazinocarbonylmethoxy-N-desmethyldiazepam coupled to an immunogenic carrier material such as bovine serum albumin. These antibodies can be employed in immunoassays for N-desmethyldiazepam which is a major metabolite of three important psychoactive drugs diazepam, chlordiazepoxide and clorazepate.

5 Claims, No Drawings

IMMUNOASSAY FOR N-DESMETHYLDIAZEPAM

BACKGROUND OF THE INVENTION

U.S. Pat. No. 4,046,636 disclosed enzyme conjugates of benzodiazepines useful in a homogeneous enzyme immunoassay for benzodiazepines such as oxazepam, and diazepam and chloridazepoxide. In Example 8 of this patent there is disclosed the preparation of a conjugate from N-desmethyldiazepam and bovine gamma globulin through a 3'-carboxypropyl linking group attached to the 1-position of the benzodiazepine nucleus. This material is used as an immunogen to elicit antibodies which cross-react strongly with oxazepam, diazepam and chlordiazepoxide, as well as the metabolite N-desmethyldiazepam.

U.S. Pat. Application Ser. No. 784,101 filed Apr. 4, 1977 discloses a radioimmunoassay for benzodiazepines such as diazepam, chlordiazepoxide, oxazepam, and metabolites thereof. The assay employs both known and novel antibodies. Novel antibodies are elicited using the diazonium salt of the 5-(4-aminophenyl)benzodiazepine hapten coupled to the immunogenic carrier material as the immunogen. The radioligands employed in this assay are novel $^{125}$I-labelled 4'-hydroxy derivatives of the compounds to be detected.

Peskar and Spector described a radioimmunoassay procedure useful in detecting nanogram amounts of diazepam or N-desmethyldiazepam in plasma samples in J. Pharmacol Exp. Ther. 186, 167 (1973). This assay utilized $^{14}$C-diazepam as the tracer. Antibodies were elicited using either 5-[3-(4-aminophenylazo)-4-hydroxy-phenyl]-7-chloro-1,3-dihydro-1-methyl-2H-1,4-benzodiazepin-2-one or 7-amino-5-(2-chlorophenyl)-3H-1,4-benzodiazepin-2(1H)-one as haptens which were subsequently coupled to bovine serum albumin (BSA) to form the desired immunogens.

Dixon et al. reported in J. Pharm. Sci. 64, 937 (1975) of a radioimmunoassay for chlordiazepoxide in plasma. Once again the tracer compound was a $^{14}$C-labelled compound. The immunogen was derived by coupling the reactive acyl azide of 7-chloro-5-(4-hydrazinocarbonylmethoxyphenyl)-2-methylamino-3H-1,4-benzodiazepine-4-oxide to BSA.

Spin labelling of benzodiazepines for use in a Free Radical Assay Technique is disclosed by Goldstein et al. in U.S. Pat. No. 3,690,834. Specific benzodiazepines disclosed include chlordiazepoxide, diazepam and oxazepam.

Another paper by Dixon et al., J. Pharm. Sci. 66 235 (1977) describes a radioimmunoassay for clonazepam using an immunogen consisting of 3-hemisuccinoyloxyclonazepam covalently bound to BSA. The tracer employed for the assay was $^3$H-clonazepam.

DESCRIPTION OF THE INVENTION

The present invention relates to an improved immunoassay which is highly specific for N-desmethyldiazepam, a major metabolite of several important benzodiazepine therapeutic agents such as chlordiazepoxide, diazepam and clorazepate. The high specificity of the present assay method stems from the use of highly specific antibodies to N-desmethyldiazepam. Such antibodies are elicited by using as an immunogen the novel hapten 4'-hydrazino-carbonylmethoxy-N-desmethyldiazepam covalently coupled to an immunogenic carrier material.

In a preferred embodiment of the present invention a radioimmunoassay for N-desmethyldiazepam is disclosed which is simple, specific and sensitive. Such radioimmunoassay permits a limit of sensitivity of about 10 ng/ml of N-desmethyldiazepam in 0.05 ml of unextracted plasma or blood. Moreover, due to the high specificity exhibited by the aforesaid antibodies the radioimmunoassay provided less than 1% cross-reaction with a number of possible interfering compounds such as diazepam, chlordiazepoxide, clonazepam and amitriptyline. Finally, good agreement ($r=0.99$) was obtained for the plasma and blood levels of N-desmethyldiazepam in subjects receiving diazepam or clorazepate when samples were assayed by the radioimmunoassay of the present invention and an established electron-capture gas-chromatography (EC-GC) technique.

Although a number of EC-GC techniques are known in the art for the determination of N-desmethyldiazepam in plasma either of the intact molecule or, following acid hydrolysis, of 2-amino-5-chlorobenzophenone and while such methods have the necessary sensitivity to determine therapeutic levels of N-desmethyldiazepam they are time consuming in comparison to the high through-put that can be achieved with RIA procedures. A further advantage of the immunoassay of the present invention is that it can be utilized for routine clinical analysis of plasma or whole blood without the necessity for extraction.

The radioimmunoassay of the present invention utilizes radiolabelled derivatives of N-desmethyldiazepam as tracers. Suitable radiolabelled derivatives include $^3$H, $^{14}$C and $^{125}$I-labelled N-desmethyldiazepam prepared in accordance with procedures well-known in the art. A preferred tracer compound is $^3$H-N-desmethyldiazepam which is conveniently prepared from N-desmethyldiazepam by catalytic exchange using a rhodium on alumina catalyst.

Novel antibodies useful in the present radioimmunoassay are obtained by utilizing an immunogen prepared by covalently coupling 4'-hydrazinocarbonylmethoxy-N-desmethyldiazepam to a conventional immunogenic carrier material and immunizing a suitable host animal with the immunogen.

Conventional immunogenic carrier materials useful in the practice of the present invention include those materials which have the property of independently eliciting an immunogenic response in a host animal and which can be coupled to the aforesaid hapten. Suitable carrier materials include, for example, proteins, natural or synthetic polymeric compounds such as polypeptides, e.g., polylysine or copolymers of amino acids; polysaccharides; and the like. Particularly preferred carrier materials are proteins and polypeptides, especially proteins.

The identity of the protein material used in the preparation of the nitrogen of the instant invention is not critical. Examples of suitable proteins useful in the practice of this invention include mammalian serum proteins such as, for example, human gamma globulin, human serum albumin, bovine serum albumin (BSA), methylated bovine serum albumin, rabbit serum albumin and bovine serum globulin. Bovine serum albumin is a preferred protein material. Other suitable protein materials will be suggested to one skilled in the art. It is generally preferred but not critically necessary that protein materials be utilized which are foreign to the animal hosts in which the resulting antigen will be employed.

The hapten, 7-chloro-1,3-dihydro-5-(4-hydrazinocarbonyl-methoxyphenyl)-2H-1,4-benzodiazepin-2-one, can be converted to a reactive acyl azide by treatment with nitrous acid and covalently coupled to the immunogenic carrier material by a method analogous to that described by Dixon et al., J., Pharm. Sci. 64, 937 (1975) so as to prepare the desired antigen.

The antigens hereinabove described may be utilized to induce formation of the desired specific antibodies in host animals by injecting the antigen in such a host animal, preferably using an adjuvant. Improved titers can be obtained by repeated injections over a period of time. Suitable host animals for this purpose include mammals such as rabbits, horses, goats, guinea pigs, rats, cows, sheep, etc. Rabbits are a preferred host animal. The resulting antisera will contain antibodies which will selectively complex with N-desmethyldiazepam. If desired, the antibodies can be purified and/or isolated from the antisera using procedures well-known in the art. Such procedures include precipitation, column chromatography, gel chromatography, electrophoresis and the like.

The antibodies described above are useful as reagents for the determination of N-desmethyldiazepam concentrations in biological fluids preferably in plasma or whole blood. In one useful assay procedure, a known amount of labelled N-desmethyldiazepam is mixed with the above antibody and a sample containing an unknown concentration of N-desmethyldiazepam is added. The amount of N-desmethyldiazepam in the sample can be determined by measuring the inhibition of the binding to the specific antibody of the labelled N-desmethyldiazepam by the sample compound and comparing the value observed with a standard curve previously developed. The reagents may be added in any order. A suitable assay procedure for this purpose is described in greater detail in U.S. Pat. No. 3,709,868. Other assay procedures known in the art for carrying out radioimmunoassays can also be employed.

The present invention is further illustrated in the following Examples:

EXAMPLE 1

Materials and Methods

Synthesis of Tracer:

Tritium labelled N-desmethyldiazepam was prepared by catalytic exchange with tritium gas using rodium catalyst on alumina. The crude material was purified by column chromatography on silica gel and had a specific activity of 9.5 mCi/mg.

Synthesis of Immunogen:

The hapten, 7-chloro-1,3-dihydro-5-(4-hydrazinocarbonylmethoxyphenyl)-2H-1,4-benzodiazepin-2-one was prepared from 7-chloro-1,3-dihydro-5-(4-hydroxyphenyl)-2H-1,4-benzodiazepin-2-one by an analogous procedure employed by Dixon et al. supra in the preparation of 7-chloro-5(4-hydrazinocarbonylmethoxyphenyl)-2-methylamino-3H,-1,4-benzodiazepine 4-oxide, and was converted to its reactive acyl azide with nitrous acid and covalently coupled to bovine serum albumin by the procedure of Dixon et al. supra. It was estimated, by means of differential pulse polarography, that the immunogen consisted of 15 moles of hapten covalently coupled to 1 mole of albumin.

Immunization:

Two New Zealand white rabbits were immunized by intradermal injection of the immunogen as an emulsion in Freund's complete adjuvant (1 mg/ml) using the protocol of Dixon et al. supra. The animals were then boosted at monthly intervals by intravenous and subcutaneous injection of 100 µg of the immunogen as a solution in isotonic saline via both routes. Serum was harvested at 10 to 14 days following each booster and stored at −20° C.

RIA Procedure:

The assay was carried out in 12×75 mm glass tubes using 0.01 M Tris buffer (pH 7.5) containing 0.9% NaCl and 0.1% sodium azide. A calibration curve was generated by addition of $^3$H-N-desmethyldiazepam (15,000 cpm) in 0.5 ml of buffer to tubes containing 0.5 to 20 ng of unlabelled N-desmethyldiazepam in 50 µl of control plasma or blood followed by 0.4 ml of suitably diluted antiserum. Appropriate controls were included to determine nonspecific (i.e. absence of antiserum) and specific binding of the tracer. Following incubation at room temperature for 0.5 to 1 hr, an equal volume (1 ml) of saturated ammonium sulfate (adjusted to pH 7.5 with 5 N NaOH) was added to precipitate antibody-bound radioligand. The mixture was vortexed and after standing for 10 min at 4° C. in a refrigerated centrifuge, the tubes were centrifuged at 2500×g for 20 min. The supernate was removed by aspiration and the precipitate, containing the antibody-bound radioligand, dissolved in 0.4 ml of water. (When whole blood samples were assayed, the precipitate was washed twice with 1 ml of 50% saturated ammonium sulfate prior to its dissolution in water. This procedure removed virtually all of the heme proteins which might otherwise interfere with the subsequent liquid scintillation counting procedure.) After the addition of 3 ml of Aquasol (New England Nuclear, Boston, Mass. 02118) each tube was vortexed *immediately* to give a clear solution, capped with a Caplug (size 5X, Protective Closures Co., Inc., Buffalo, N.Y. 14207) and the tube counted directly as described by Dixon and Cohen, Clin. Chem, 22, 1746 (1976) in a modified liquid scintillation counter (Packard Tri-Carb, Model 3255, Packard Instrument Co., Ill. 60515). The counting efficiency for tritium under these conditions was 32%.

All samples were assayed in duplicate and the data calculated as outlined by Robard, Clin. Chem. 20, 1255 (1970) using a digital computer for iterative weighted linear regression analysis of logit $B/B_o$ versus log dose where B and $B_o$ are the amounts of antibody-bound radioligand in the presence and absence of unlabelled drug, respectively. Both B and $B_o$ were corrected for nonspecific binding.

The intra- and inter-assay precision was determined by repetitive analysis of 8 different patient plasma samples over a period of several weeks.

The specificity of the RIA was established by determination of the extent of cross-reactivity of a number of potential competitors with the antiserum and by comparison of the RIA method with the EC-GC procedure of de Silva et al., Anal. Chem. 48, 10 (1976).

Plasma and blood samples:

Plasma samples were obtained from normal volunteers and psychiatric patients who had been receiving 15 to 85 mg/day of diazepam chronically. Whole blood samples were obtained from two volunteers who had ingested a single 15 mg dose of clorazepate.

RESULTS AND DISCUSSION

The presence of antibodies to N-desmethyldiazepam was shown in both rabbits 6 weeks following the initial immunization as evidenced by binding of $^3$H-N-desmethyldiazepam. However, a maximum titer was not reached until after the second booster immunization when 0.5 μl of antiserum bound approximately 50% of the added radioligand.

A typical calibration curve, when logit $B/B_o$ was plotted versus the log concentration of unlabelled N-desmethyldiazepam in plasma, demonstrated that the response was linear from 0.5 to 20 ng; the 0.5 ng standard produced greater than 10% inhibition of binding of the radioligand to the antiserum. The calibration curve obtained in whole blood was virtually identical. Thus 10 ng/ml of N-desmethyldiazepam could be readily determined using a 50 μl sample of plasma or whole blood. However, for routine analysis of N-desmethyldiazepam in the clinical situation, such sensitivity is unnecessary and a 10 μl sample is more suitable giving a range of 50 to 2000 ng/ml. For levels in excess of 2 μg/ml the sample is appropriately diluted with control plasma or blood prior to analysis.

The intra- and inter-assay coefficients of variation did not exceed 5.8 and 11.1% respectively over a range of 0.26 to 5.06 μg/ml of N-desmethyldiazepam.

The antiserum exhibited a high degree of specificity of N-desmethyldiazepam as evidenced by its low cross-reactivity with a number of potential competitors listed in Table 1.

TABLE 1

Cross-reactivity of Potential Competitors with the Antiserum to N-desmethyldiazepam

| Compound | % Cross-reaction* |
|---|---|
| N-desmethyldiazepam | 100 |
| Clorazepate | >50 |
| Diazepam | 0.6 |
| Chlordiazepoxide | 0.2 |
| N-desmethylchlordiazepoxide | 0.8 |
| Demoxepam | 0.6 |
| Oxazepam | 5.5 |
| Clonazepam | 0.3 |
| 7-Aminoclonazepam | 0.07 |
| Amitriptyline | <0.01 |
| Nortriptyline | <0.01 |

*Determined at 50% inhibition of antibody-bound $^3$H-N-desmethyldiazepam.

Although clorazepate apparently showed greater than 50% cross-reactivity, this was undoubtedly due, in part, to its decarboxylation to N-desmethyldiazepam during the assay incubation period at physiological pH. With this consideration in mind and in view of the recent report that some intact clorazepate reaches the circulation and may amount to 7 to 20% of the N-desmethyldiazepam blood concentration for up to 12 hr following clorazepate administration, the present RIA would tend to over estimate the actual in vivo levels of N-desmethyldiazepam in blood samples taken during this time.

Oxazepam, which showed 5.5% cross-reaction, would not be a problem in the analysis of clinical samples, since, although a urinary metabolite of diazepam and clorazepate, it is only present in negligible quantities in plasma. However a false positive level of N-desmethyldiazepam would be encountered in the blood of subjects receiving oxazepam although N-desmethyldiazepam is not a metabolite but a precursor, of the drug. Diazepam, which is a precursor of N-desmethyldiazepam exhibited only 0.5% cross-reactivity. Similarly, chlordiazepoxide and its plasma metabolites, N-desmethylchlordiazepoxide and demoxepam, all showed less than 1% cross-reactivity. Similarly, the anti-convulsant, clonazepam and the anti-depressant, amitriptyline, both of which might be concomitantly administered with diazepam, chlordiazepoxide or clorazepate, showed negligible interference.

Further evidence for the specificity of the RIA was obtained by comparison with an established EC-GC method for the determination of N-desmethyldiazepam. The joint determinations for 11 blood samples from clorazepate-treated subjects over a range of 24–205 ng/ml and 19 plasma samples from diazepam-treated subjects over a range of 312–6400 ng/ml were pooled and subjected to straight line analysis by the method of Wald using a 95% confidence elipse. The correlation coefficient was 0.998 and the regression line had a slope of 107 with a y intercept of −5.8 over the almost 300-fold range. Thus the RIA method can measure N-desmethyldiazepam as precisely as the EC-GC procedure.

In summary, the present RIA for N-desmethyldiazepam is simple, specific and sensitive and offers an attractive alternative to the more time consuming EC-GC procedures for multiple sample analysis and/or where limited sample volumes are available.

EXAMPLE 2

2-Amino-5-chloro-4'-hydroxybenzophenone

To a solution of 83.7 g (0.34 mole) of 5-chloro-3-(4-hydroxyphenyl)-2,1-benzisoxazole in 1500 ml of glacial acetic acid was added 45 g of iron filings. The mixture was stirred and heated on the steam bath for 20 min. Every 30 min. an additional 20 g of iron filings and 100 ml of water was added for 2.5 hr. After 30 min. more, the reaction mixture was filtered while hot. The collected precipitate was heated with acetic acid and filtered. The combined filtrates were diluted with ice water to precipitate 39.8 g (47%) of product, mp 170°–175°. Recrystallization from methanol-water gave yellow rods, mp 173°–178°.

EXAMPLE 3

2-Bromo-4'-chloro-2'-(4-hydroxybenzoyl)acetanilide

A solution of 41 g (0.165 mole) 2-amino-5-chloro-4'-hydroxybenzophenone in 800 ml of ether and 200 ml of water was cooled to 5°. The mixture was stirred while 20 ml (0.277 mole) of bromoacetyl bromide and a 20% solution of sodium carbonate were added alternately keeping the solution slightly basic. After 20 min. the reaction mixture was filtered to collect 60 g (about 100%) of product mp 201°–202°. Recrystallization from ethanol gave colorless prisms, mp 201°–203°.

Anal.-Calc. for $C_{15}H_{11}BrClNO_3$: C, 48.87; H, 3.01, Tot.hal., 31.30. Found: C, 49.17; H, 3.34; Tot.hal., 3084.

EXAMPLE 4

7-Chloro-1,3-dihydro-5-(4-hydroxyphenyl)-2H-1,4-benzodiazepin-2-one

To 350 ml of liquid ammonia was added 60 g (0.163 mole) of 2-bromo-4'-chloro-2'-(4-hydroxybenzoyl)acetanilide. After refluxing for 3 hr, the ammonia was allowed to evaporate. The residue was heated to reflux in 400 ml of ethanol for 3 hr. Ethanol was evaporated, and 800 ml of acetone was added. This suspension was heated and filtered to remove inorganic salts. Concentration of acetone filtrate gave 31.5 g (67%) of product, mp 271°–272°.

Anal.Calc. for $C_{15}H_{11}ClN_2.O_2$: C, 62.84; H, 3.87; N, 9.77; Found C, 62.52; H, 4.13, N, 9.92.

I claim:

1. A composition consisting essentially of the reaction product of the reactive acyl azide of 7-chloro-1,3-dihydro-5-(4-(hydrazinocarbonylmethoxyphenyl)-2H-1,4-benzodiazepin-2-one and an immunogenic carrier material.

2. The composition of claim 1 wherein said immunogenic carrier material is bovine serum albumin.

3. An antibody specific to N-desmethyldiazepam, said antibody being prepared by innoculating a host animal with an immunogen comprising the reaction product of claim 1 to elicit said antibody in the serum of said host animal and collecting serum from said host animal.

4. An improved method for the radioimmunoassay of N-desmethyldiazepam in a sample which method comprises mixing said sample with a known amount of radiolabelled N-desmethyldiazepam compound and the antibody of claim 3, measuring the degree of binding of the said radiolabelled N-desmethyldiazepam to said antibody, and determining the amount of said N-desmethyldiazepam in said sample by comparing said degree of binding to a standard curve.

5. The method of claim 4 wherein said radiolabelled N-desmethyldiazepam compound is $^3$H-desmethyldiazepam.

* * * * *